(12) United States Patent
Yamamoto et al.

(10) Patent No.: US 10,105,041 B2
(45) Date of Patent: Oct. 23, 2018

(54) LIGHT GUIDING OPTICAL SYSTEM AND ENDOSCOPIC APPARATUS HAVING THE SAME

(71) Applicant: CANON KABUSHIKI KAISHA, Tokyo (JP)

(72) Inventors: Akira Yamamoto, Ageo (JP); Hidetoshi Sato, Sanda (JP)

(73) Assignee: CANON KABUSHIKI KAISHA, Tokyo (JP)

(*) Notice: Subject to any disclaimer, the term of this patent is extended or adjusted under 35 U.S.C. 154(b) by 230 days.

(21) Appl. No.: 14/706,324

(22) Filed: May 7, 2015

(65) Prior Publication Data
US 2015/0327756 A1  Nov. 19, 2015

(30) Foreign Application Priority Data
May 15, 2014 (JP) ................. 2014-101163

(51) Int. Cl.
*A61B 1/06* (2006.01)
*A61B 1/07* (2006.01)
(Continued)

(52) U.S. Cl.
CPC .............. *A61B 1/07* (2013.01); *A61B 1/0017* (2013.01); *A61B 1/0661* (2013.01);
(Continued)

(58) Field of Classification Search
CPC ................ A61B 18/20; A61B 18/24; A61B 2018/00172; A61B 2018/00642;
(Continued)

(56) References Cited

U.S. PATENT DOCUMENTS 4,805,984 A * 2/1989 Cobb, Jr. ............... G02B 5/12
359/592
5,204,931 A 4/1993 Gehringer et al.
(Continued)

FOREIGN PATENT DOCUMENTS

JP    S53005886 A    1/1978
JP    S56145866 A    11/1981
(Continued)

OTHER PUBLICATIONS

English translation of Office Action issued in Japanese Application No. 2014-101163 dated Mar. 20, 2018.
(Continued)

*Primary Examiner* — John P Leubecker
*Assistant Examiner* — Pamela F Wu
(74) *Attorney, Agent, or Firm* — Rossi, Kimms & McDowell LLP

(57) ABSTRACT

A light guiding optical system includes a light guide configured to guide light from an entrance end to an exit end by internally reflecting the light a plurality of times, and an optical unit configured to condense the light emitted from the exit end of the light guide in a first section. The exit end of the light guide has an aperture that has a size in a first direction perpendicular to the first section, which is larger than a size in a second direction perpendicular to the first direction.

16 Claims, 4 Drawing Sheets

(51) Int. Cl.
*G02B 23/24* (2006.01)
*G02B 27/09* (2006.01)
*A61B 1/00* (2006.01)
*F21V 8/00* (2006.01)

(52) U.S. Cl.
CPC ....... *G02B 23/243* (2013.01); *G02B 23/2469* (2013.01); *G02B 27/0911* (2013.01); *G02B 6/0008* (2013.01); *G02B 6/0096* (2013.01)

(58) Field of Classification Search
CPC .. A61B 2018/00982; A61B 2018/2035; A61B 2018/2211; A61B 2018/2244; A61B 1/06; A61B 1/0607; A61B 1/0676; A61B 1/0684; A61B 1/07; A61B 2090/306; A61B 1/0661; G02B 23/2461; G02B 23/2469; G02B 6/4296
USPC .......................................... 600/160, 176–178
See application file for complete search history.

(56) References Cited

U.S. PATENT DOCUMENTS

| | | | | |
|---|---|---|---|---|
| 5,566,267 | A | * | 10/1996 | Neuberger ........ C03B 37/01493 385/123 |
| 8,362,448 | B2 | | 1/2013 | Wolleschensky et al. |
| 2006/0222298 | A1 | * | 10/2006 | Hatori .................. G02B 6/1228 385/43 |
| 2007/0091425 | A1 | | 4/2007 | Kawano |
| 2009/0237765 | A1 | * | 9/2009 | Lippert .................. G02B 21/06 359/213.1 |
| 2012/0098949 | A1 | | 4/2012 | Knebel et al. |

FOREIGN PATENT DOCUMENTS

| | | |
|---|---|---|
| JP | S56163665 A | 12/1981 |
| JP | S58159738 A | 9/1983 |
| JP | S59198404 A | 11/1984 |
| JP | S62213748 A | 9/1987 |
| JP | H05080217 A | 4/1993 |
| JP | 10104523 A | 4/1998 |
| JP | 2002288644 A | 10/2002 |
| JP | 2006243306 A | 9/2006 |
| JP | 2007114542 A | 5/2007 |
| JP | 2008250303 A | 10/2008 |
| JP | 2011511966 A | 4/2011 |
| JP | 2011167328 A | 9/2011 |
| JP | 2012108491 A | 6/2012 |

OTHER PUBLICATIONS

Office Action issued in Japanese Application No. 2014-101163 dated Mar. 20, 2018.

* cited by examiner

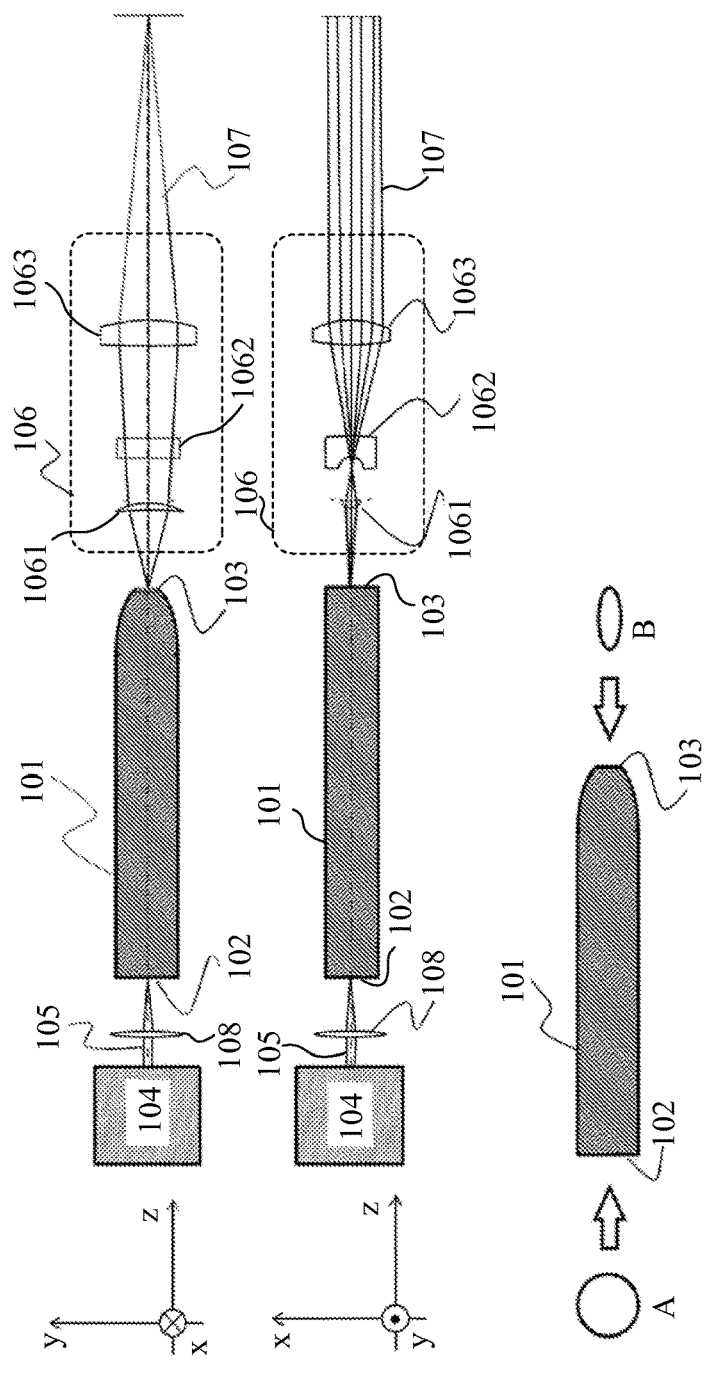

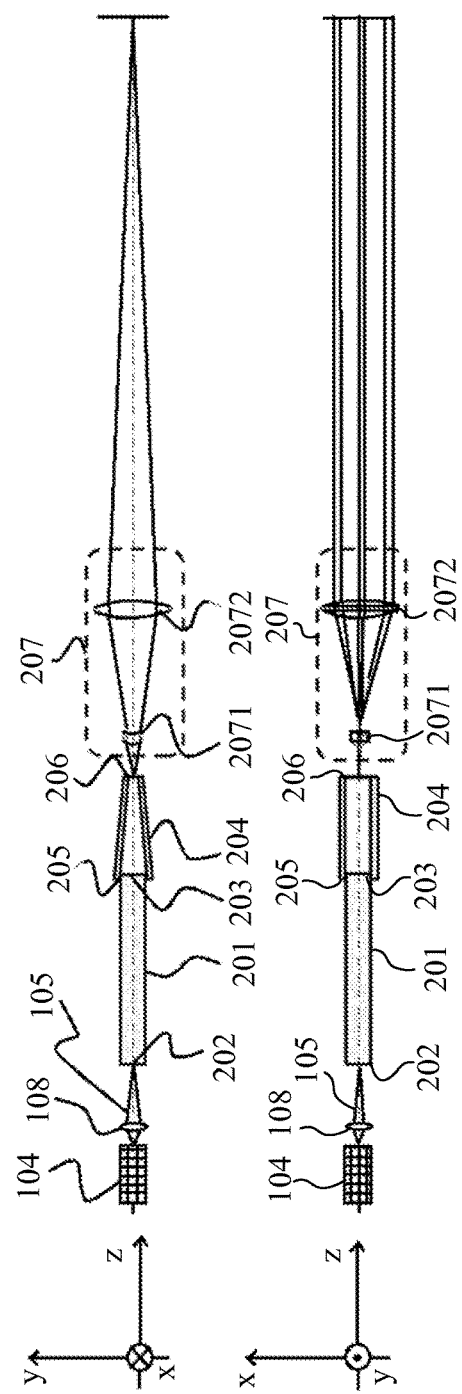

LIGHT GUIDING OPTICAL SYSTEM AND ENDOSCOPIC APPARATUS HAVING THE SAME

BACKGROUND OF THE INVENTION

Field of the Invention

The present invention relates generally to a light guiding optical system, and more particularly to a light guiding optical system that can be installed in an endoscopic apparatus configured to acquire an image of an internal structure of a target to be observed.

Description of the Related Art

Each of Japanese Patent Laid-Open Nos. ("JPs") 2012-108491 and 2007-114542 discloses a microscope configured to provide three-dimensional Raman imaging of a target to be observed. The microscope disclosed in each of JPs 2012-108491 and 2007-114542 generates a sheet shaped beam ("sheet beam" hereinafter) from near an infrared laser beam using a galvano scanner, and introduces the sheet beam into the target in a direction orthogonal to an observation direction. Thereby, the Raman scattering occurs only in a sheet shaped area onto which excited light is irradiated, and the internal structure of the target can be visualized.

An endoscope structure rather than the microscope structure is necessary to acquire an image of the internal structure of the organism, and it is also necessary to introduce a laser beam as excited light to a point near the target. JP 2006-243306 discloses a method for guiding a laser beam using a hollow fiber. Since no Raman scattering occurs in the hollow fiber, the hollow fiber applied to the endoscope can reduce noises caused by the Raman scattering in observing the target.

However, the microscope disclosed in each of JPs 2012-108491 and 2007-114542 generates a sheet beam using a galvano scanner rather than measuring each organic tissue in vivo, and it is thus difficult to apply the methods in these references to the endoscope that requires a small structure and thin diameter. In addition, a hollow part as a core in the hollow fiber becomes very thick due to the manufacturing characteristic. A fiber end surface becomes a secondary light source in generating a sheet beam when the hollow fiber is applied to the endoscope. As a result, a large image is formed near the sheet beam focal point, the sheet beam becomes thick, and the resolution remarkably decreases particularly in the observation direction (or depth direction in the observation).

SUMMARY OF THE INVENTION

The present invention provides a light guiding optical system and an endoscopic apparatus having the same, each of which is small and advantageous to a sheet beam generation.

A light guiding optical system according to the present invention includes a light guide configured to guide light from an entrance end to an exit end by internally reflecting the light a plurality of times, and an optical unit configured to condense the light emitted from the exit end of the light guide in a first section. The exit end of the light guide has an aperture that has a size in a first direction perpendicular to the first section, which is larger than a size in a second direction perpendicular to the first direction.

Further features of the present invention will become apparent from the following description of exemplary embodiments with reference to the attached drawings.

BRIEF DESCRIPTION OF THE DRAWINGS

FIGS. 1A to 1C are views illustrating a laser transmitter according to a first embodiment of the present invention.

FIGS. 2A and 2B are views illustrating a laser transmitter according to a second embodiment of the present invention.

DESCRIPTION OF THE EMBODIMENTS

Figure 3A:
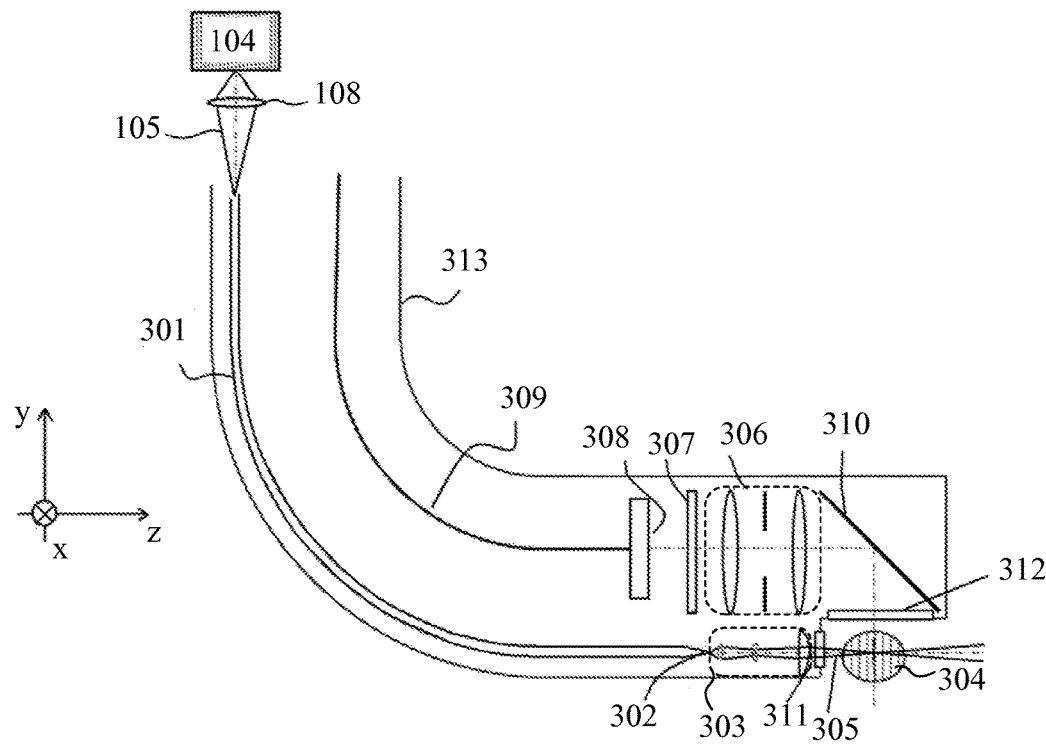
FIGS. 3A and 3B are views illustrating an endoscope apparatus according to a third embodiment of the present invention.

The present invention relates to an endoscopic apparatus configured to illuminate a target (object) to be observed and to enable the target to be observed. Known illustrative endoscopes include a medical endoscope used for an observation, diagnosis, and medical treatment of an internal organs, and an industrial endoscope used for an observation and repair of a location that is hard to observe, such as the interior of a pipe and an aperture in the unit in the machine or equipment. Many of these endoscope are used for an observation of a surface shape of a target, and have difficulties, for example, in visualizing an internal lesion etc. even with a short distance from the surface. On the other hand, methods that use near infrared light as excited light, such as the Raman spectral imaging and fluorescent imaging, can acquire data of the internal organs because the near infrared light deeply enters the internal organs and a wavelength different from that of the excited light can be used for the detection. A detailed description will be given of embodiments of the endoscope apparatus according to the present invention.

First Embodiment

Referring to FIGS. 1A to 1O, a description will be given of a first embodiment of the present invention. FIGS. 1A to 1O illustrate a laser transmitter according to this embodiment. FIG. 1A is a yz sectional view of a hollow fiber in the laser transmitter. FIG. 1B is its xz sectional view. FIG. 1O is an explanatory view of a shape of the hollow fiber 101. As illustrated in FIG. 1O, an entrance side aperture 102 of the hollow fiber 101 has a shape of a circle A and an exit side aperture 103 thereof has a shape of an ellipse B. Therefore, the shape of the hollow fiber 101 has sectional shapes as illustrated in FIGS. 1A and 1B. The aperture shape of the exit side aperture 103 is not limited to the ellipse, such as a rectangle, as long as a size in a predetermined direction (first direction or x direction) may be larger than a size in a direction (second direction or y direction) perpendicular to the predetermined direction.

In this embodiment, the x direction (first direction) is a direction in which the exit side aperture 103 has the longest width. Thus, the exit end of the hollow fiber has an aperture that is larger in the first direction (x direction) perpendicular to the yz section (first section) than in the second direction (y direction) perpendicular to the x direction (or xz section (second section)).

A laser beam 105 emitted from a laser light source 104 enters the entrance end 102 of the hollow fiber 101 via a coupling optical system 108. The laser beam 105 passes the inside of the hollow fiber 101, and is emitted from the exit end 103 of the hollow fiber 101. Thus, the hollow fiber 101 serves as a light guide configured to guide light emitted from the laser light source 104, from the entrance end to the exit end. The laser beam emitted from the exit end 103 of the hollow fiber 101 enters a sheet beam generating optical system 106. The sheet beam generating optical system 106 includes three anamorphic lenses 1061, 1062, and 1063.

The sheet beam generating optical system 106 according to this embodiment includes three lenses but the present invention allows the sheet beam generating optical system 106 to include at least two lenses. The sheet beam generating optical system 106 converts the laser beam 105 into a sheet shaped light (sheet beam) 107 which is a converged beam on the yz section and a parallel beam on the xz section, and emits from the sheet beam generating optical system 106. In other words, the sheet beam generating optical system 106 converts the laser beam 105 into the converged beam on the yz section that is a plane parallel to the y direction and the parallel beam on the xz section parallel to the x direction. In other words, the sheet beam generating optical system 106 serves as an optical unit configured to diverge the light emitted from the hollow fiber 101 in the predetermined direction (x direction) so as to convert that light into a parallel beam (diverging light), and to convert that light into the converged light in the direction (y direction) orthogonal to the predetermined direction.

Thus, in this embodiment, the sheet beam generating optical system 106 serves to condense, on the yz section (first section), the light emitted from the exit end of the hollow fiber 101. The optical unit is arranged so that the direction (x direction of the xz section) in which the laser beam diverges accords with the direction (x direction) in which the exit side aperture 103 has the largest width rather than the direction (y direction) orthogonal to the direction in which the exit side aperture 103 has the largest width. In other words, the optical unit is arranged so that the direction (y direction of the yz section) in which the laser beam is converged accords with the direction (y direction) orthogonal to the x direction in which the exit side aperture 103 has the largest width. In other words, the exit end of the hollow fiber has an aperture that has a size in the x direction (first direction) perpendicular to the yz direction (first section) in which the laser beam is converged, which is larger than a size in the y direction (second direction) perpendicular to the x direction.

The above directional accordance is satisfied both by a perfect accordance and by an approximate accordance within a tolerance of a margin of error. The coupling optical system 108, the hollow fiber 101, and the sheet beam generating optical system 106 constitute an optical system configured to emit light from the laser light source 104 to the object.

In general, the hollow fiber 101 has a very large core diameter (at the hollow part), for example, between 0.3 mm to 1 mm. Therefore, when the optical system is arranged so as to generate the sheet beam 107, a large light source image is formed near the focal point of the optical system. For example, when the core diameter of the hollow fiber (size of the secondary light source) is 0.3 mm, the exit NA is 0.07, the thickness of the sheet beam 107 (spot diameter) is 50 µm for $1/e^2$ of the peak intensity value, and a wavelength is 800 nm, the image side NA necessary for the optical system is given as follows:

Image side $NA$=(spot diameter/1.64/wavelength)$^{-1}$*0.5=(50/1.64/0.8)$^{-1}$*0.5= 0.01312

Therefore, the magnification M of the optical system becomes as follows:

$M$=0.07/0.01312=5.33

An image size I formed on the fiber end surface as the secondary light source formed by the sheet beam generating optical system 106 becomes as follows:

$I$=0.3*5.33=1.599 mm

In order to make a spot of 50 µm, an image exceeding 1.5 mm is formed and thus the sheet beam 107 becomes thicker.

Accordingly, the shape of the exit end aperture 103 of the hollow fiber 101 is narrowed in one direction. By so doing, the image size is reduced, the exit NA is made larger, and the fine spot can be easily formed. For example, in FIG. 1A, when the diameter of the exit side aperture 103 is 2 µm and the exit side NA is 0.2, the magnification M' of the optical system and the size I' of the image on the fiber end surface are expressed as follows:

$M'$=0.2/0.01312=15.24

$I'$=2*15.24=30.48 µm

Thereby, the image size becomes smaller than spot diameter, and a very thin sheet beam 107 can be generated.

As illustrated in FIG. 1B, the parallel beam is emitted on the xz section and does not contribute to the image size. It is therefore unnecessary to reduce the size of the fiber exit side aperture 103 as the secondary light source unlike its size on the yz section.

The sheet beam generating optical system 106 needs to have an effect of imaging light on the yz section and an effect of emitting a parallel beam on the xz section. The parallel beam is necessary to make the intensity in the sheet beam 107 as uniform as possible. Since the exit side aperture 103 is large on the xz section, the sheet beam generating optical system 106 may emit light as telecentric as possible on the xz section.

For the above effects, the lens 1061 in the sheet beam generating optical system 106 which is located closest to the light source may have a positive optical power (inverse of the focal length). By so doing, the diameter of the laser beam divergently emitted from the hollow fiber 101 is narrowed and the lens outer diameter can be reduced.

Moreover, the lens 1061 closest to the light source is a lens having a toric surface or an anamorphic surface which satisfies P2>P1, where P1 is an optical power on the yz section illustrated in FIG. 1A (perpendicular to a surface of the sheet beam 107) and P2 is an optical power on the xz section illustrated in FIG. 1B (parallel to the surface of the sheet beam 107). In other words, the lens closest to the light guide in the sheet beam generating optical system 106 has positive optical powers both on the yz section (first section) and on the xz section (second section). At least two surfaces in the lenses in the sheet beam generating optical system 106 according to the present invention have different optical powers between the yz section (first section) and the xz section (second section). For a telecentric emission on the xz section, the surface on the image side of the lens 1063 that is closest to the image is a toric surface or an anamorphic surface having a positive optical power P3 on the xz section. In other words, the lens farthest from the light guide in the sheet beam optical system 106 has a positive optical power on the xz section (second section). In addition, the lens farthest from the light guide in the sheet beam optical system 106 has a positive optical power on the yz section (first section). Due to P2>P1, the primary imaging is made on the xz section in the sheet beam optical system 106.

The imaging point is positioned near a synthesized focal point of the lenses closer to the image than the imaging point (or near the focal point of the lens 1063 in this embodiment). Due to this optical power arrangement, the converged beam can be emitted on the yz section and the parallel beam can be telecentrically emitted on the xz section.

Glass materials used for the sheet beam generating optical system 106 and the coupling optical system 108 may be made of a single composition, such as synthesized quartz and sapphire. This is because the normal optical glass contains many components, and the Raman scattered light emitted from the glass material causes noises in the observation.

FIGS. 1A to 1C illustrate the hollow fiber thicker than the lens diameters for better understanding. The actual diameter of the hollow fiber is smaller than actual. This is true of the following other figures.

The thin sheet beam can be generated by narrowing the exit end of the hollow fiber in one direction. The sheet beam generating optical system that has at least two toric or anamorphic surfaces can generate a sheet beam with a simple structure. Since no scanner, such as a galvanometer, is used, the sheet beam can be generated by a small structure that has no moving unit.

This embodiment provides the exit end of the hollow fiber with an aperture that is wide in one direction and narrow in another direction, and thereby reduces the image and thins the sheet beam in the narrow direction of the aperture as the secondary light source. In addition, the sheet beam generating optical system can be made small and efficient because it is arranged so that the in-plane direction of the sheet beam accords with the direction in which the exit end aperture is wide.

Second Embodiment

Referring to FIGS. 2A and 2B, a description will be given of a second embodiment of the present invention. The second embodiment provides an exit end of a hollow fiber with a separate member configured to narrow the exit aperture. Those elements in FIGS. 2A and 2B, which are corresponding elements in FIGS. 1A to 1C, are designated by the same reference numerals, and a detailed description thereof will be omitted. In the following figures, those elements designated by the same reference numerals have the same effects. FIG. 2A is a yz sectional view of a laser transmitter, and FIG. 2B is its xz sectional view.

As illustrated in FIGS. 2A and 2B, a laser beam 105 emitted from a laser light source 104 enters an entrance end 202 of a hollow fiber 201 via the coupling optical system 108. The entrance side aperture 202 and an exit side aperture 203 of the hollow fiber 201 are circular and have the same size. This embodiment attaches a tapered member 204 to the exit side aperture 203. In this embodiment, the hollow fiber 201 and the tapered member 204 serve as a light guide configured to guide light from the laser light source 104, and to guide the light from the entrance end 202 to the exit end 206 of the tapered member 204. One end surface 205 of the tapered member 204 is adjacent to the exit side aperture 203, and has almost the same size as that of the exit side aperture 203. An end surface 206 on the opposite side has a rectangular aperture in which one side is shorter than the other side. Even in this embodiment, the exit side aperture of the light guide has such a shape that a size in the predetermined direction (first direction or x direction) may be larger than a size in the direction (second direction or y direction) perpendicular to the predetermined direction.

This configuration can more easily narrows the aperture of the hollow fiber in one direction than working part of a long hollow fiber. However, due to the discontinuity between the hollow fiber 201 and the tapered member 204, this embodiment increases a loss of light quantity in comparison with the first embodiment.

Assume that the rectangle has a short side of 2 μm (on the yz section in FIG. 2A) and a long side of 200 μm (on the xz section in FIG. 2B), the hollow fiber (size of the secondary light source) has a core diameter of 200 μm, a working wavelength is 850 nm, the thickness of the sheet beam 107 (beam diameter on the short side direction) is 20 μm, and the exit NA in the short side direction is 0.2. Then, the necessary image side NA is as follows:

Image side $NA = (20/1.64/0.85)^{-1} * 0.5 = 0.03485$

The magnification M2 of the optical system is as follows:

$M2 = 0.2/0.03485 = 5.73$

The image size I on the fiber end surface as the secondary light source formed by a sheet beam generating optical system 207 is as follows:

$I = 0.002 * 5.73 = 0.01146$ mm $= 11.46$ μm

The size of the image in the short side direction is equal to or smaller than the spot diameter. Thereby, a thin sheet beam can be generated using the above structure.

Similar to the first embodiment, a lens 2071 closest to the light source in the sheet beam generating optical system 207 according to this embodiment has a positive optical power. In addition, P2'>P1' is satisfied, where P1' is a power of the lens 2071 on the yz section having the short side direction of the end surface 206 of the tapered member 204, and P2' is a power of the lens 2071 on the xz section having the long side direction. The lens 2072 closest to the image has a toric or anamorphic surface on the image side having a positive optical power P3' on the section having the long side direction of the tapered member 204.

The sheet beam generating optical system includes three lenses in the first embodiment, and two lenses in the second embodiment. However, the number of lenses is not limited as long as the optical system includes two or more lenses.

This embodiment provides the exit end (of the tapered member) of the hollow fiber with the aperture that is wide in one direction and narrow in another direction, thereby reducing the size of the image in the narrow direction of the aperture as the secondary light source, thinning the sheet beam, and preventing the resolution drop in the depth direction. In addition, the sheet beam generating optical system can be made small and efficient because it is arranged so that the in-plane direction of the sheet beam accords with the direction in which the exit end aperture is wide.

Third Embodiment

Figure 3B:
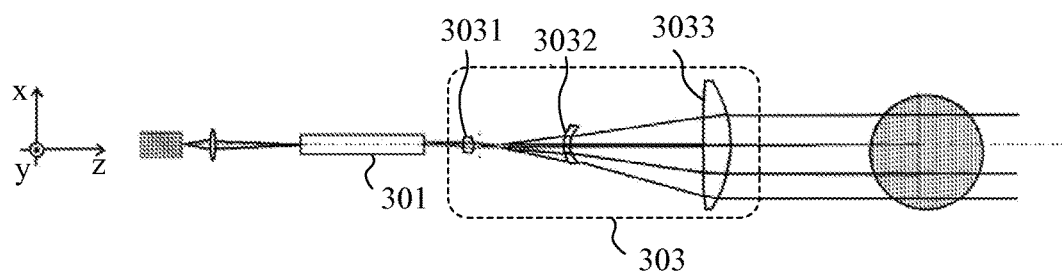

Referring to FIGS. 3A and 3B, a description will be given of a third embodiment according to the present invention. FIGS. 3A and 3B illustrate one exemplary structure of an endoscopic apparatus 313 that includes as an illumination optical system a laser transmitter according to the present invention. FIG. 3A is a yz sectional view of the endoscopic apparatus, and FIG. 3B is an xz sectional view of the sheet beam generating optical system 303 and a hollow fiber 301.

The laser beam 105 emitted from the laser light source 104 enters the hollow fiber 301 via the coupling optical system 108. The exit end of the hollow fiber 301 has an elliptical aperture 302 that is narrowed in the y direction, similar to the first embodiment. The laser beam 105 emitted from the elliptical aperture 302 of the hollow fiber 301 enters the sheet beam generating optical system 303, is emitted as a sheet beam 305 that is converged on the yz section in FIG. 3A and is parallel on the xz section in FIG. 3B, transmits a window 311, and enters a target 304. The sheet beam generating optical system 303 includes three lenses 3031, 3032, and 3033. Details of these lenses 3031, 3032, and 3033 will be described with reference to FIG. 6 and Tables 3-1 and 3-2.

The target 304 (object) generates Raman scattered light only in an area irradiated by a sheet beam 305, and the Raman scattered light transmits a window 312 and enters the observation optical system. The observation optical system is arranged so that the optical axis crosses the sheet beam 305. The observation optical system includes a reflective surface 310, an image-pickup optical system 306, and a filter 307, and the Raman scattered light emitted from the target 304 forms an image on the image sensor 308. The formed image is converted into the electric signal by the image sensor 308, and sent to the outside via a cable 309 so as to obtain a two-dimensional Raman image. In this embodiment, the image sensor 308 serves as an acquirer configured to acquire information of an image formed by the observation optical system. For the acquirer, an entrance end of a fiber bundle may be arranged instead of the image sensor 308. The fiber bundle acquires information of the image formed by the observation optical system, and sends the information to the outside of the endoscopic apparatus 313.

Due to this configuration, direct scattered light of the sheet beam 305 as excited light is hard to enter the image-pickup optical system 306, a selective excitation on a specific plane is available, and a high resolution image can be obtained in the depth direction of the image-pickup optical system 306. A three-dimensional Raman imaging can be built by moving the target 304 relative to the sheet beam 305 in the optical-axis direction of the image-pickup optical system 306 and by acquiring the Raman image at each position.

A two-dimensional Raman image can be acquired by a small structure by combining the laser transmitter and the observation optical system according to the present invention. A three-dimensional Raman image can be obtained by moving the target relative to the sheet beam.

This embodiment can provide a light guiding optical system and an endoscopic apparatus having the same, each of which has a small configuration and is advantageous to sheet beam generations.

NUMERICAL EXAMPLES

Numerical examples 1 to 3 correspond to the sheet beam generating optical systems according to the first to third embodiments.

The present invention uses a non-rotationally symmetrical surface referred to as an anamorphic surface for the sheet beam generating optical system. This surface is defined as Expression 1. The coordinate system has a three-dimensional coordinate axes of a z-axis, a y-axis and an x-axis.

The z-axis is defined as a line that passes a center (origin of the absolute coordinate) of the first surface from the center of a 0-th surface (OBJ) and this direction is set to be positive.

The y-axis is defined as a line that passes the center (origin of the absolute coordinate) of the first surface, and forms a right angle relative to the z-axis in the counterclockwise direction.

The x-axis is defined as a line that is perpendicular to both the z-axis and the y-axis.

$$z = \frac{CUXx^2 + CUYy_i^2}{1 + \{1 - (1+KX)CUX^2x^2 - (1-KY)CUY^2y^2\}^{1/2}} +$$
$$AR\{(1-AP)x^2 + (1+AP)y^2\}^2 +$$
$$BR\{(1-BP)x^2 + (1+BP)y^2\}^3 +$$
$$CR\{(1-CP)x^2 + (1+CP)y^2\}^4 +$$
$$DR\{(1-DP)x^2 + (1+DP)y^2\}^5$$

EXPRESSION 1

Herein, k is a conic coefficient. CUX/CUY is a curvature (inverse of the radius of curvature R) in each of the XY directions. Tables 1-2, 2-2, 3-2 indicate values of each of the coefficients k, AR-DR, and AP-DP. In Tables 1-1, 2-1, and 3-1, a blank column means a spherical surface shape, and AAS means that an aspheric surface shape. A surface in which all of k, AR-DR, and AP-DP are 0 is a toric surface, and expressed by TOR.

The rotationally symmetrical spherical surface is defined as Expression 2.

$$Z = \frac{cr^2}{1 + \sqrt{(1+k)c^2r^2}} + Ar^4 + Br^6 + Cr^8 + Dr^8$$

EXPRESSION 2

Figure 4:
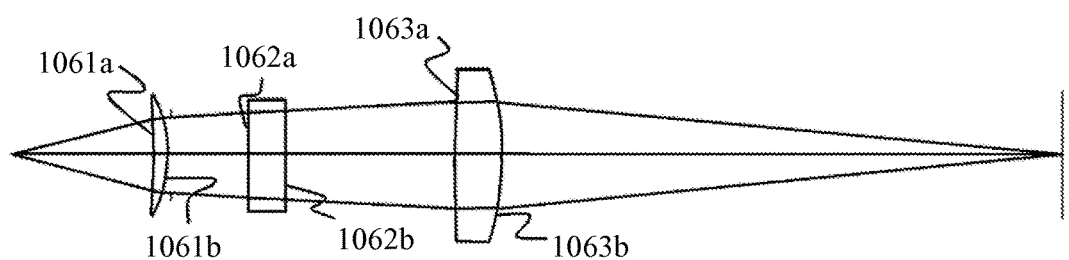
FIG. 4 is a sectional view of a sheet beam generating optical system according to the first embodiment.
Figure 5:
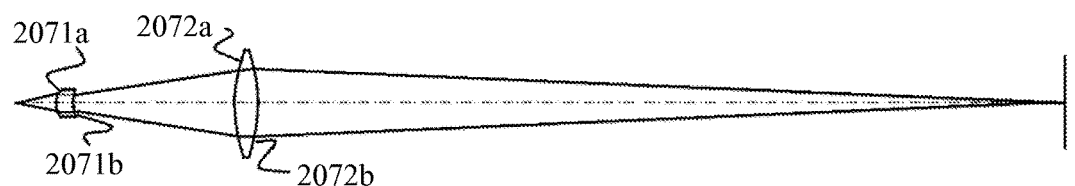
FIG. 5 is a sectional view of a sheet beam generating optical system according to the second embodiment.
Figure 6:
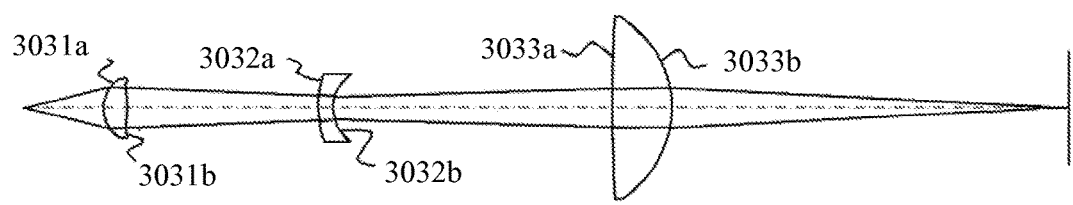
FIG. 6 is a sectional view of a sheet beam generating optical system according to the third embodiment.

Similar to the non-rotationally symmetrical aspheric surface, a surface shape of rotationally symmetrical aspheric surface is expressed as AL in Table 2-1. N780 is a refractive index for light having a wavelength of 780 nm. FIGS. 4 to 6 illustrate components corresponding to surface numbers in each Table. Each figure illustrates a yz section of the sheet beam generating optical system in the corresponding numerical example. Numerical values of powers P1, P2, and P3 of the lens and surface in each numerical example will be also illustrated.

Numerical Example 1

The incident NA on the optical system is 0.2 on the xz section and 0.07 on the yz section, and a target spot size is 50 μm on the yz section.

TABLE 1-1

| No. | Type | Rx | Ry | D | N780 |
|---|---|---|---|---|---|
| OBJ | | 0.0000 | 0.0000 | 5.1851 | |
| 1061a | TOR | 0.7265 | −24.8354 | 0.5000 | 1.453317 |
| 1061b | AAS | 2.3869 | −3.2077 | 0.1000 | |
| STO | | | | 2.8121 | |
| 1062a | TOR | −0.8634 | 33.1374 | 1.3895 | 1.453317 |
| 1062b | AAS | −10.1489 | −61.9580 | 6.1258 | |
| 1063a | TOR | 14.9312 | 42.8561 | 1.6993 | 1.453317 |
| 1063b | TOR | −5.3914 | −7.4870 | 20.3283 | |
| IMG | | | | | |

TABLE 1-2

|  | KX | KY | AR | BR | AP | BP |
|---|---|---|---|---|---|---|
| 1061b | 0.0000 | 0.0000 | −3.4573E−08 | 1.4205E−04 | 145.8410 | 7.8132E−01 |
|  | KX | KY | AR | BR | AP | BP |
| 1062b | 0.0000 | 0.0000 | 1.0767E−05 | 5.2379E−05 | −13.6270 | −3.6964E−08 |

P1=0.1237
P2=0.4739
P3=0.0839

Numerical Example 2

The incident NA on the optical system is 0.2 on the xz section and 0.05 on the yz section, and a target spot size is 20 μm on the yz section.

TABLE 2-1

| No. | Type | Rx | Ry | D | N780 |
|---|---|---|---|---|---|
| OBJ |  | 0.0000 | 0.0000 | 2.6553 |  |
| 2071a | AL | 1.2204 | 1.2204 | 1.0600 | 1.453317 |
| 2071b | AAS | −0.3282 | 1.7321 | 0.1110 |  |
| STO |  |  |  | 9.7818 |  |
| 2072a | AL | 8.8921 | 8.8921 | 1.4113 | 1.453317 |
| 2072b | AAS | −8.8197 | −10.7443 | 49.4824 |  |
| IMG |  |  |  |  |  |

TABLE 2-2

|  | K | A | B |  |  |  |
|---|---|---|---|---|---|---|
| 2071a | 0.0000 | −4.3357E−04 | −2.7961E−03 |  |  |  |
|  | KX | KY | AR | BR | AP | BP |
| 2071b | 18.5675 | −0.8148 | 2.6998E−06 | −7.0342E−03 | −251.1560 | −0.7813 |
|  | K | A | B |  |  |  |
| 2072a | 0.0000 | −4.1961E−04 | −4.2960E−05 |  |  |  |
|  | KX | KY | AR | BR | AP | BP |
| 2072b | −1.4270 | 0.0465 | −1.4520E−09 | −9.6334E−06 | 40.9024 | 0.1348 |

P1=0.1802
P2=1.3764
P3=0.0513

Numerical Example 3

The incident NA on the optical system is 0.25 on the xz section and 0.07 on the yz section, and a target spot size is 100 μm on the yz section.

TABLE 3-1

| No. | Type | Rx | Ry | D | N780 |
|---|---|---|---|---|---|
| OBJ |  | 0.0000 | 0.0000 | 2.8025 |  |
| 3031a |  | 1.50717 | 1.50717 | 0.8000 | 1.453317 |
| 3031b | AAS | −0.7593 | −4.0644 | 0.4382 |  |
| STO |  |  |  | 6.2486 |  |
| 3032a | TOR | 1.8921 | 4.5614 | 0.5000 | 1.453317 |
| 3032b |  | 1.6925 | 1.6925 | 9.7360 |  |
| 3033a |  | 60.5364 | 60.5364 | 2.0627 | 1.453317 |
| 3033b | TOR | −8.2070 | −4.4511 | 13.8383 |  |
| IMG |  |  |  |  |  |

TABLE 3-2

|  | KX | KY | AR | BR | AP | BP |
|---|---|---|---|---|---|---|
| 3031b | 0.0000 | 0.0000 | 0.0862 | 0.0224 | 0.0000 | 0.0000 |

P1=0.3938
P2=0.7989
P3=0.0552

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

For example, the light guide may be a solid optical fiber instead of the hollow optical fiber. In addition, the sheet beam generating optical system may simply collimate the light in the X direction without causing the light to diverge. Moreover, the sheet beam generating optical system may simply diverge the light in X direction without converting the diverging light into a parallel beam.

This application claims the benefit of Japanese Patent Application No. 2014-101163, filed May 15, 2014, which is hereby incorporated by reference herein in its entirety.

What is claimed is:

1. A light guiding optical system comprising:
a light guide configured to guide light from an entrance end of the light guide to an exit end of the light guide by internally reflecting the light a plurality of times; and
an optical unit including a plurality of lenses configured to condense the light emitted from the exit end in a first section of a cross-section of the exit end, the first section including an optical axis of the optical unit,
wherein the exit end has an aperture that has a larger size in a first direction perpendicular to the first section than in a second direction perpendicular to a second section of the cross-section of the exit end, the second section perpendicular to the first section and including the optical axis,
wherein the exit end aperture has a size in the second direction that is smaller than a size of an aperture of the entrance end in the second direction,
wherein a lens closest to the light guide among the plurality of lenses has positive powers both in the first section and the second section of the cross-section, and an optical power that has a size in the second section larger than a size in the first section, and
wherein the light from the exit end of the light guide enters the lens closest to the light guide among the plurality of lenses without entering any other intervening lens.

2. The light guiding optical system according to claim 1, wherein the optical unit converts the light from the light guide into diverging light on the second section.

3. The light guiding optical system according to claim 1, wherein the optical unit converts the light from the light guide into parallel light on the second section.

4. The light guiding optical system according to claim 1, wherein the optical unit has a lens surface that has different powers between the first section and the second section.

5. The light guiding optical system according to claim 4, wherein the optical unit includes a plurality of lens surfaces.

6. The light guiding optical system according to claim 1, wherein a lens farthest from the light guide among the plurality of lenses has a positive power in the first section.

7. The light guiding optical system according to claim 1, wherein the light guide is an optical fiber.

8. The light guiding optical system according to claim 7, wherein the light guide is a hollow fiber.

9. The light guiding optical system according to claim 1, wherein the optical unit forms a primary image in the optical unit in the second section.

10. The light guiding optical system according to claim 9, wherein the optical unit telecentrically emits the light emitted from the exit end in the second section.

11. The light guiding optical system according to claim 1, wherein a size of the aperture of the exit end in the first direction is larger than or equal to that of the entrance end in the first direction.

12. An endoscopic apparatus comprising:
   a light guiding optical system configured to irradiate light onto an object;
   an observation optical system configured to form an image of the object; and
   an acquirer configured to acquire information of the image of the object formed by the observation optical system,
   wherein the light guiding optical system includes:
      a light guide configured to guide light from an entrance end of the light guide to an exit end of the light guide by internally reflecting the light a plurality of times; and
      an optical unit including a plurality of lenses configured to condense the light emitted from the exit end in a first section of a cross-section of the exit end, the first section including an optical axis of the optical unit,
      wherein the exit end has an aperture that has a larger size in a first direction perpendicular to the first section than in a second direction perpendicular to a second section of the cross-section of the exit end, the second section perpendicular to the first section and including the optical axis,
      wherein the exit end aperture has a size in the second direction that is smaller than a size of an aperture of the entrance end in the second direction,
      wherein a lens closest to the light guide among the plurality of lenses has positive powers both in the first section and the second section of the cross-section, and an optical power that has a size in the second section larger than a size in the first section, and
      wherein the light from the exit end of the light guide enters the lens closest to the light guide among the plurality of lenses without entering any other intervening lens.

13. The endoscopic apparatus according to claim 12, wherein an optical axis of the observation optical system crosses light emitted from the optical unit.

14. The endoscopic apparatus according to claim 12, wherein the acquirer is an image sensor.

15. The endoscopic apparatus according to claim 12, wherein the observation optical system guides Raman scattering light emitted from the object to the acquirer.

16. A light guiding optical system comprising:
   a light guide including an entrance end and an exit end configured to guide light from the entrance end to the exit end by internally reflecting the light a plurality of times; and
   an optical unit including a plurality of lenses arranged along an optical axis configured to condense the light from the exit end,
   wherein the entrance end is an isotropic aperture having an entrance end aperture size and the exit end is an anisotropic aperture having a first exit end aperture size in a first direction perpendicular to the optical axis and a second exit end aperture size in a second direction perpendicular to the first direction,
   wherein the first exit end aperture size is larger than the second exit end aperture size and the second exit end aperture size is smaller than the entrance end aperture size,
   wherein the entrance end aperture size is substantially the same as the first exit end aperture size, and
   wherein a proximal lens closest to the light guide among the plurality of lenses has positive powers both in the first direction and the second direction, and an optical power of the proximal lens in the second direction is larger than that in the first direction.

* * * * *